(12) United States Patent
Kerr, II

(10) Patent No.: US 7,413,544 B2
(45) Date of Patent: Aug. 19, 2008

(54) SYSTEM AND METHOD FOR COLLECTING AND TRANSMITTING MEDICAL DATA

(76) Inventor: Robert A. Kerr, II, 446 Catalina Dr., Newport Beach, CA (US) 92663

( * ) Notice: Subject to any disclaimer, the term of this patent is extended or adjusted under 35 U.S.C. 154(b) by 531 days.

(21) Appl. No.: 11/222,157

(22) Filed: Sep. 7, 2005

(65) Prior Publication Data

US 2006/0010040 A1    Jan. 12, 2006

Related U.S. Application Data

(62) Division of application No. 10/636,164, filed on Aug. 6, 2003, now Pat. No. 6,942,616, which is a division of application No. 09/724,721, filed on Nov. 28, 2000, now Pat. No. 6,612,984.

(60) Provisional application No. 60/168,942, filed on Dec. 3, 1999.

(51) Int. Cl.
*A61B 5/00* (2006.01)
*G06F 13/00* (2006.01)

(52) U.S. Cl. ..................... 600/300; 600/323

(58) Field of Classification Search ............... 600/300, 600/323, 301, 903, 904, 920
See application file for complete search history.

(56) References Cited

U.S. PATENT DOCUMENTS

| 5,549,117 | A | 8/1996 | Tacklind et al. |
| 5,626,144 | A | 5/1997 | Tacklind et al. |
| 5,704,366 | A | 1/1998 | Tacklind et al. |
| 5,857,967 | A | 1/1999 | Frid et al. |
| 5,889,474 | A | 3/1999 | LaDue |
| 5,951,300 | A | 9/1999 | Brown |
| 5,987,519 | A | 11/1999 | Peifer et al. |
| 5,997,476 | A | 12/1999 | Brown |

(Continued)

FOREIGN PATENT DOCUMENTS

WO    WO 9824212    4/1995

(Continued)

OTHER PUBLICATIONS

Website: Fitsense, www.fitsense.com.

(Continued)

*Primary Examiner*—Daniel L Robinson
(74) *Attorney, Agent, or Firm*—Orrick, Herrington & Sutcliffe LLP

(57) ABSTRACT

A system and method for collecting and transmitting medical and health-related data over a network are disclosed. A measuring device measures a user's physiological attribute and produces a first signal related thereto, which an integration system coupled to the measuring device receives and converts into a second signal for transmitting over the Internet. In accordance with one aspect of a preferred embodiment, the integration system is adapted to read the first signal as it is sent from the measuring device to its display. A communications system transmits the second signal over the Internet to a remote system using any of a variety of techniques known in the art. The remote system extracts the measured physiological attribute and other associated data from the second signal and populates a database. Preferably, a web-based portal provides access to the data for one or more users.

14 Claims, 3 Drawing Sheets

U.S. PATENT DOCUMENTS

| | | | |
|---|---|---|---|
| 6,013,007 | A | 1/2000 | Root et al. |
| 6,024,699 | A | 2/2000 | Surwit et al. |
| 6,035,328 | A | 3/2000 | Soukal |
| 6,095,985 | A | 8/2000 | Raymond et al. |
| 6,101,478 | A | 8/2000 | Brown |
| 6,122,351 | A | 9/2000 | Schlueter, Jr. et al. |
| 6,148,342 | A | 11/2000 | Ho |
| 6,151,586 | A | 11/2000 | Brown |
| 6,159,147 | A | 12/2000 | Lichter et al. |
| 6,162,180 | A | 12/2000 | Miesel et al. |
| 6,168,563 | B1 | 1/2001 | Brown |
| 6,264,614 | B1 | 7/2001 | Albert et al. |
| 6,304,788 | B1 | 10/2001 | Eady et al. |
| 6,312,378 | B1 | 11/2001 | Bardy |
| 6,336,900 | B1 | 1/2002 | Alleckson et al. |
| 6,350,237 | B1 | 2/2002 | Pelletier et al. |
| 6,421,633 | B1 | 7/2002 | Heinonen et al. |
| 6,612,984 | B1 * | 9/2003 | Kerr, II ............ 600/300 |
| 6,942,616 | B2 * | 9/2005 | Kerr, II ............ 600/300 |
| 2001/0047125 | A1 | 11/2001 | Quy |
| 2001/0051787 | A1 | 12/2001 | Haller et al. |
| 2001/0056229 | A1 | 12/2001 | Consentino et al. |
| 2002/0052542 | A1 | 5/2002 | Bardy |

FOREIGN PATENT DOCUMENTS

| | | |
|---|---|---|
| WO | WO 9824358 | 6/1998 |
| WO | WO 9859487 | 12/1998 |
| WO | WO 9914882 | 3/1999 |
| WO | WO 0049549 | 8/2000 |
| WO | WO 0052604 | 9/2000 |

OTHER PUBLICATIONS

Website: Hommed, www.hommed.com.
Website: LifeChart, www.lifechart.com.
Website: LifeLink, www.llmi.com.
Website: Sensatex, www.sensatex.com.
Website: Sportbrain, www.sportbrain.com/products/essentials.cfm.
Website: StayHealthy, www.stayhealthy.com.
Website: Sunbeam, http://www.thaliaproducts.com/.
Barro, S. et al., "Intelligent Telemonitoring of Critical-Care Patients," IEEE Engr Med Biol., Jul./Aug. 1999, pp. 80-88.
Hutten, H. et al., "Cardiac Telemonitoring By Integrating Pacemaker Telemetry Within Worldwide Data Communication Systems," Proc. 19$^{th}$ Intl. Conf. IEEE/EMBS Oct. 30-Nov. 2, 1997, pp. 974-976.
Lee, H., et al., "Real-Time Monitoring Service Through World-Wide Web," Proc. 19$^{th}$ Intl Conf, IEEE/EMBS Oct. 30-Nov. 2, 1997, pp. 928-931.
Magrabi, F. et al., "Web Based Longitudinal ECG Monitoring," Proc. of 20$^{th}$ Intl Conf IEEE Bed Biol Soc., vol. 20, No. 3, 1998, p. 1155-1158.
Nelwan, S. et al., "Ubiquitous Access to Real-Time Patient Monitoring Data," Computers in Cardiology vol. 24, 1997.
Park, S. et al., "Real-Time Monitoring of Patients on Remote Sites," Proc. of 20$^{th}$ Intl Conf IEEE Med Biol Soc., vol. 20, No. 3, 1998, pp. 1321-1325.
Singh, S. et al., "Internet Based Infant Monitoring System," Proc. of 1$^{st}$ Joint BMES/EMBS Conf., Oct. 13-16, 1999, p. 674.
Vagas, J.E., "Home-Based Monitoring of Cardiac Patients," Info Tech Apps. Biomed, Proc. 1998 IEEE Intl Conf., May 16-17, 1998.
Online search: warfarin (Coumadin)—drug class, medical uses, medication side effects, and drug interactions, Description of Warfarin, Written by Pharmacists, Reviewed by Doctors http://www.medicinenet.com/warfarin/article.htm 10/31/2005, pp. 1-3 pages.

* cited by examiner

SYSTEM AND METHOD FOR COLLECTING AND TRANSMITTING MEDICAL DATA

RELATED APPLICATION INFORMATION

This application is a divisional of U.S. patent application Ser. No. 10/636,164, filed on Aug. 6, 2003 and issued as U.S. Pat. No. 6,942,616, which is a divisional of U.S. patent application Ser. No. 09/724,721, filed on Nov. 28, 2000 and issued as U.S. Pat. No. 6,612,984, which is based on U.S. Provisional Patent Application Ser. No. 60/168,942, filed on Dec. 3, 1999.

BACKGROUND OF THE INVENTION

The invention relates to systems for collecting and transmitting medical and health-related data over a network.

The healthcare industry is the largest sector of this nation's economy, comprising over one trillion dollars, or roughly 13% of the gross domestic product (GDP). Because of increasing healthcare costs, it is desirable to reduce overhead, free hospitals beds, and increase compliance with treatment. Remote medical data monitoring devices are directed precisely at those goals.

Accordingly, advances in healthcare and medical devices are increasingly required to meets the needs of an aging population. For example, medical industry experts predict that the demand for medical data monitoring systems will drastically increase over the next decade. Existing monitoring systems, however, fall short of satisfying customers' needs in several ways.

Some remote monitoring systems have been designed to allow patients to transmit their medical data from their homes. An example of one such monitoring system provides a measuring device, such as a blood sugar monitor, which a patient uses to measure a physiological attribute. The patient then enters the measurements taken by the device into the monitoring system, which transmits the data over phone lines or the Internet. Obvious drawbacks of this system are reliability of data and ease of use. Due to human error, users will sometimes enter incorrect data. Because it is not connected to the measuring device, the monitoring system is incapable of detecting or correcting the error, and the database is therefore corrupted. Further, it is inconvenient, and perhaps difficult for some users, to manually enter data. Other existing devices are inadequate because they are not easily expanded, cannot work with multiple users or devices, or are encumbered by physical wire connections.

SUMMARY OF THE PREFERRED EMBODIMENTS

Accordingly, a system for collecting and transmitting medical and health-related data over a network is provided. In one preferred embodiment, the system comprises a measuring device that measures a physiological attribute and produces a first signal related thereto, an integration system coupled to the measuring device that receives the first signal from the measuring device and converts it into a second signal for transmitting over the Internet, a communications system that transmits the second signal over the Internet, and a remote system that receives the second signal. In accordance with one aspect of the preferred embodiment, the integration system is adapted to read the first signal as it is sent from the measuring device to its display. In accordance with one aspect of the preferred embodiment, the remote system extracts the measured physiological attribute from the second signal and populates a database with that data. In accordance with another aspect of the preferred embodiment, a web-based portal is provided for accessing the database over the Internet.

In another preferred embodiment, a method is disclosed for collecting and transmitting medical and health-related data over a network. The method includes the steps of collecting the data by sensing an electrical signal from a measuring device, converting the electrical signal for transmitting over the network, and transmitting the data to a remote system.

In another preferred embodiment, several measuring devices are adapted to measure physiological attributes and produce corresponding signals relating thereto, an integration system receives the signals and converts them into a format that a communications system transmits over the network, and a remote system coupled to the network receives the data. In accordance with one aspect of the preferred embodiment, the signals include unique user identifiers that associate each datum with an individual user, thereby allowing the system to maintain data for multiple users and multiple devices.

Other aspects and features of the present invention will become apparent from consideration of the following description taken in conjunction with the accompanying drawings.

DETAILED DESCRIPTION OF THE PREFERRED EMBODIMENTS

A system for collecting and transmitting data over a network is herein described. In particular, the system is described as applied to the collection and transmission of medical data from one or more measuring devices; however, it will become apparent to persons skilled in the art that the teachings of this disclosure can be applied to other fields.

Figure 1:
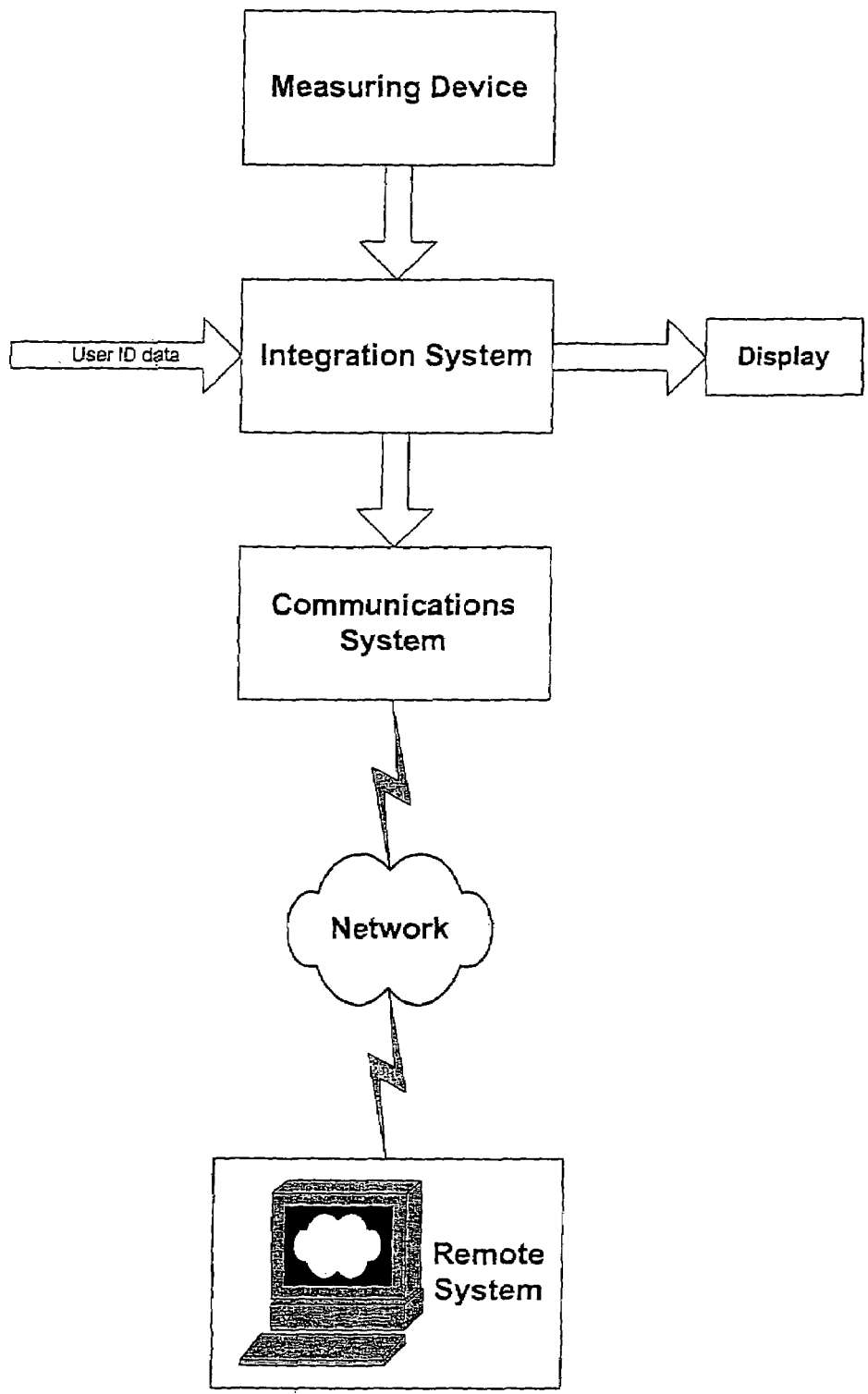
FIG. 1 is a block diagram of the system according to a preferred embodiment.

Referring to FIG. 1, a block diagram is provided showing the fundamental aspects of the system. In accordance with a preferred embodiment of the system, a measuring device, integration system, communications system, and remote system are provided. The measuring device measures a predetermined datum or data, which the integration system then acquires and formats for the communication system. The communications system provides an interface for transmitting the data across a network—e.g., the Internet—to the remote system, which then records the data for subsequent processing.

The measuring device may be any type of device that takes at least one measurement and converts it into one or more electrical signals. Preferably, the measuring device comprises a microprocessor that sends the electrical signals to a digital display, which then displays the measurement. A variety of existing medical devices can act as the measuring device in conjunction with this system, including weight scales, body fat measuring devices, blood glucose monitors, coumadin monitors, blood pressure monitors, heart rate monitors, and various fitness equipment. As well known in the art, Coumadin is the brand name for the generic drug warfarin.

Figure 2A:
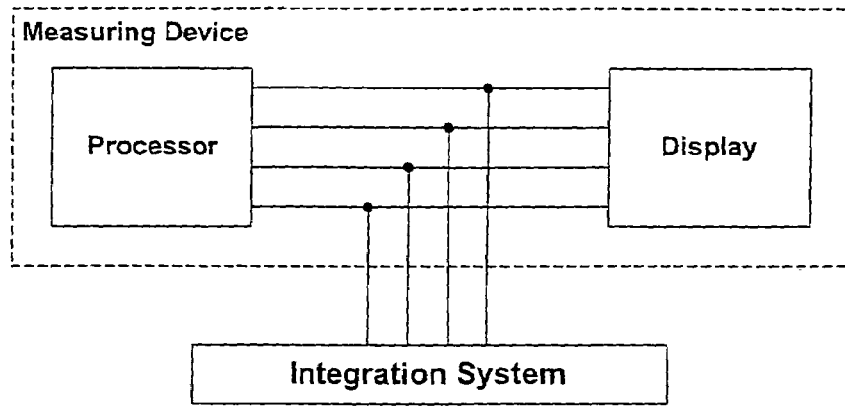
FIGS. 2a-c are block diagrams of interfaces between the measurement device and the integration system according to corresponding preferred embodiments.

The integration system is specifically adapted to acquire the measurement from the particular measuring device. As the types of measuring devices that may be used with this system vary, so do the possible techniques for acquiring data from the measuring devices. One method of capturing data from the measuring devices is illustrated in FIG. 2a, in which the measuring device comprises a processor and a digital display. The processor and display are electrically coupled by a plurality of lines, the number of lines being dictated by the design of the measuring device. In the embodiment shown in FIG. 2a, the integration system is connected to the measuring device in parallel with the microprocessor and display. The integrated system can thus "tap" into the measuring device—either from the output pins or socket of the processor, the input pins or socket of the display, or anywhere along the cable or traces between the processor and display. The integration system is preferably designed so that, when connected in parallel to the measuring device as described, it does not degrade the electrical signal and cause the display to read an incorrect value.

Figure 2B:
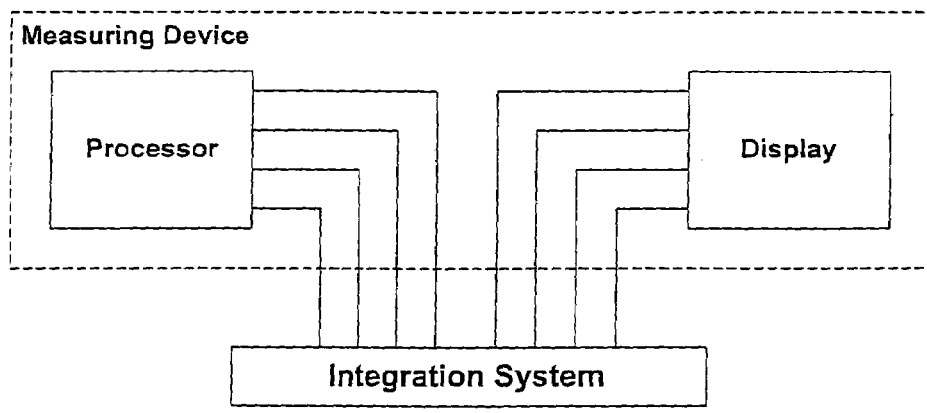
Figure 2C:
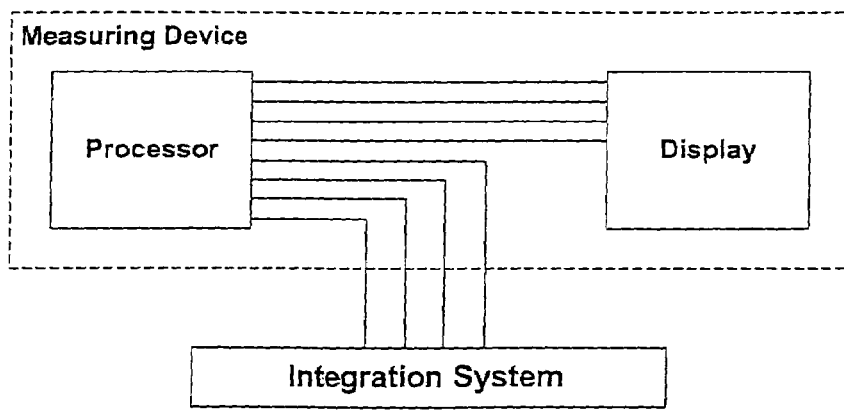

Alternatively, the integration system can be electrically coupled to the measuring device in series with the processor and display, as diagramed in FIG. 2b. In this embodiment, the integration system is adapted to receive the electrical signals directly from the processor. The integration system is further adapted to supply the electrical signals to the display of the measuring device. In accordance with yet another embodiment, shown in FIG. 2c, the display of the measuring device and the integration system are each connected directly to the processor. This method is suitable for measuring devices that include an extra port from which the data is accessible. In this embodiment, the electrical signals sent from the processor to the display may be different from those sent to the integration system.

Typically, the electrical signals tapped by the integration system as described above are multiplexed signals sent to a digital display, such as an LCD or LED display. Depending on the design of the measuring device and its display, the integration system includes hardware and/or software for determining the data from the plurality of electrical signals using techniques known in the art. For example, the integration system may include a network of logic gates for decoding and demultiplexing the signals from the digital display of the measuring device. Alternatively, the integration system can include a microprocessor programmed to decode the data from the signals. It can be appreciated that the integration system must be specifically designed for each type of measuring device because the formats of the signals will vary from device to device, and thus the algorithm for retrieving the data from the signals will likewise vary. The system is therefore highly adaptable and modular, as almost any type of electrical device can be thus tapped for its data.

Using the above techniques, the integration system can be adapted to acquire measurements from an existing OEM measuring device. In such a case, little or no modification of the OEM device's processor would be required; therefore, it is relatively easy to provide additional functionality for the system by adding different types of measuring devices. In the case of medical devices, that little or no modification of the device is required avoids certain FDA requirements for new devices, allowing the system to enter the marketplace faster. The integration system could also be designed in conjunction with a new measuring device, in which case it would be possible to provide the measuring device and integration system in one package.

In accordance with an aspect of a preferred embodiment, the integration system may also include a display for displaying the measurement that it acquired from the measuring device.

The integration system further adds data to the measurement that it retrieves from the measuring device. The integration system appends to the measurement a unique device identifier (ID). The device ID is preferably an integer, for example a six-digit number. The device ID is unique to each measuring device, and in some cases it may be read directly from the measuring device. In systems where several users share a measuring device, the integration system preferably further adds a unique user ID to the measurement and device ID, since a device ID alone would not be sufficient to associate the measurement with a particular user. The integration system may retrieve the user ID from the measuring device if available therefrom, or the user ID may be inputted directly into the integration system by the user via a programmable card swipe, keyed input, or any other means known in the art.

The integration system formats the measurement, device ID, and user ID for transmission to the communications system, to which the integration system is communicatively coupled. In accordance with a preferred embodiment, the integration system formats the measurement, device ID, and user ID as a text string. Alternatively, this data could be encoded using a standard or a proprietary algorithm. The integration system or the communications system may also add a time and date stamp to the data to indicate when the measurement was taken.

Although the integration and communication systems can be distinct systems, they may be implemented as a single unit using shared hardware and software. Further, this unit may be integral with the measuring device, as mentioned above.

The communication system formats the data received from the integration system for transmission over a network to the remote system. In a preferred embodiment, the data are sent over the Internet to the remote system. The data can be formatted in any of a variety of appropriate formats known in the art. If sent over the Internet, the data may be put into any of the established Internet communications protocols. For example, a text string containing the data could be inserted into the subject line or body of an Internet email, which would then be sent to a desired email address. Alternatively, the data could be put into a markup language such as HTML or XML, be inserted into a file sent over the network, or sent via a secure protocol such as SHTTP or SSL.

The communications system sends the formatted data to a remote system, which is also communicatively coupled to the network. In accordance with an aspect of a preferred embodiment, the remote system is programmed to determine the identity of the user to whom the measurement applies using only the device ID and/or user ID provided in the transmission. Therefore, it is unnecessary for information of a personal nature to be sent over the network. This is highly desirable in the context of, e.g., medical related data, as such information tends to be of a personal nature. While secure protocols and encryption techniques known in the art may be added to the system, the absence of personal information in the transmission obviates the need for these additional security techniques.

The communications system can be communicatively coupled to the network using a variety of methods well known in the art. Preferably, the connection to the network is effected without physical connections. Wireless communication makes the system more expandable for adding measuring devices and the like without the extra confusion of physical connections. For example, commercially available two-way pager communication systems may be used to provide the network connection interface. These commercially available systems are easily modified to interface with the integration system and may also be advantageously located within the housing of the device. The communications system may alternatively transmit the data using, e.g., Bluetooth technology or through the transmission bands of cellular phones that do not normally carry voice data. Many other techniques known in the art may also be used to transmit the data. For example, the communications system may be coupled to a computer having a communications link with the network, through, e.g., an ISDN line, cable modem, or DSL. Alternatively, the communications system may be linked to the network via a modem and phone connection. It is apparent that any of the known techniques for transmitting the data as described herein may be employed without departing from the inventive concepts of this disclosure.

Preferably, a data verification algorithm is performed to validate the integrity of the data packets as they are sent from the communications system to the remote system. One widely used technique is the Cyclic Redundancy Check (CRC). In the CRC, a number is calculated from the contents of a packet using a standard algorithm, and that number is then appended to the packet in a final field. After the packet is transmitted, the algorithm is performed on the received packet, and the numerical result is compared to the contents of the CRC field. If the calculated result is not equal to the value of the CRC field, the packet is discarded because the packet received is not identical to the packet sent. The CRC is preferred because it is a very powerful and easily implemented technique for ensuring data reliability; however, it should be understood that any known data checking technique can be used with the present system, and CRC is described by way of example.

The remote system is adapted to receive and decode the data transmitted from the communications system over the network. For example, in the case where the data is sent as a text string in the subject line of an Internet email, the remote system would first extract the string. The remote system would then parse the string to retrieve the data, which would then be placed in an appropriate database for receiving such information. The remote system could also add a time and date stamp to the data to indicate when it was received by the remote system and stored in the database. Preferably, the remote system sends a confirmation message to the communications system that indicates whether the data was received or whether it needs to be resent.

Once the measurement data collected by the remote system is inserted into one or more databases, the remote system may then provide a portal for accessing the data. In accordance with one embodiment, a computer system provides a web-based portal for viewing the data in a secure manner. To optimize performance, the portal might employ a secondary database keyed to individual users. The user or other authorized person could log into the portal using a web browser from any computer in the world connected to the Internet. By entering a user name and password, the person could access the data and any other functionality that the portal provides. Advantageously, the portal could include advertisements, and these advertisements could be highly targeted because the content of the information being accessed is known.

Referring to an example in which the data is medical related, a patient would be able to access his or her medical profile from any web browser. This medical profile would include the data measured by the medical measuring device. The profile could also be made accessible to the patient's physician, other medical personnel, and perhaps the patient's insurance company. The profile could also be tailored and formatted for which party accesses the information, as it may be desirable to limit some information provided to third parties. The patient's medical profile could be useful, e.g., in determining the patient's compliance with a prescribed medical regimen.

In one exemplary embodiment, the system is adapted to provide patients with fertility counseling. The measuring device is a fertility thermometer, and individual patients would take readings from the thermometer at regular intervals. After sufficient data is acquired by the remote system, a patient could access the portal to view her medical profile, which might include, e.g., a graph of the temperature readings over the fertility cycle. The portal might also provide the patient with counseling, such as a time period of greatest fertility during the cycle.

As explained, the system can be adapted to accommodate several measuring devices, which may be desired when a user has several physical attributes to be monitored. Also, a plurality of measuring devices serving several users would be desired in a system for monitoring the fitness progress of members of a health club. In such a system, one or more of the measuring devices would be fitness machines. The system could be adapted to provide club members with access to their individual fitness profiles using a terminal at the club or, perhaps, from their homes via the Internet.

Figure 3:
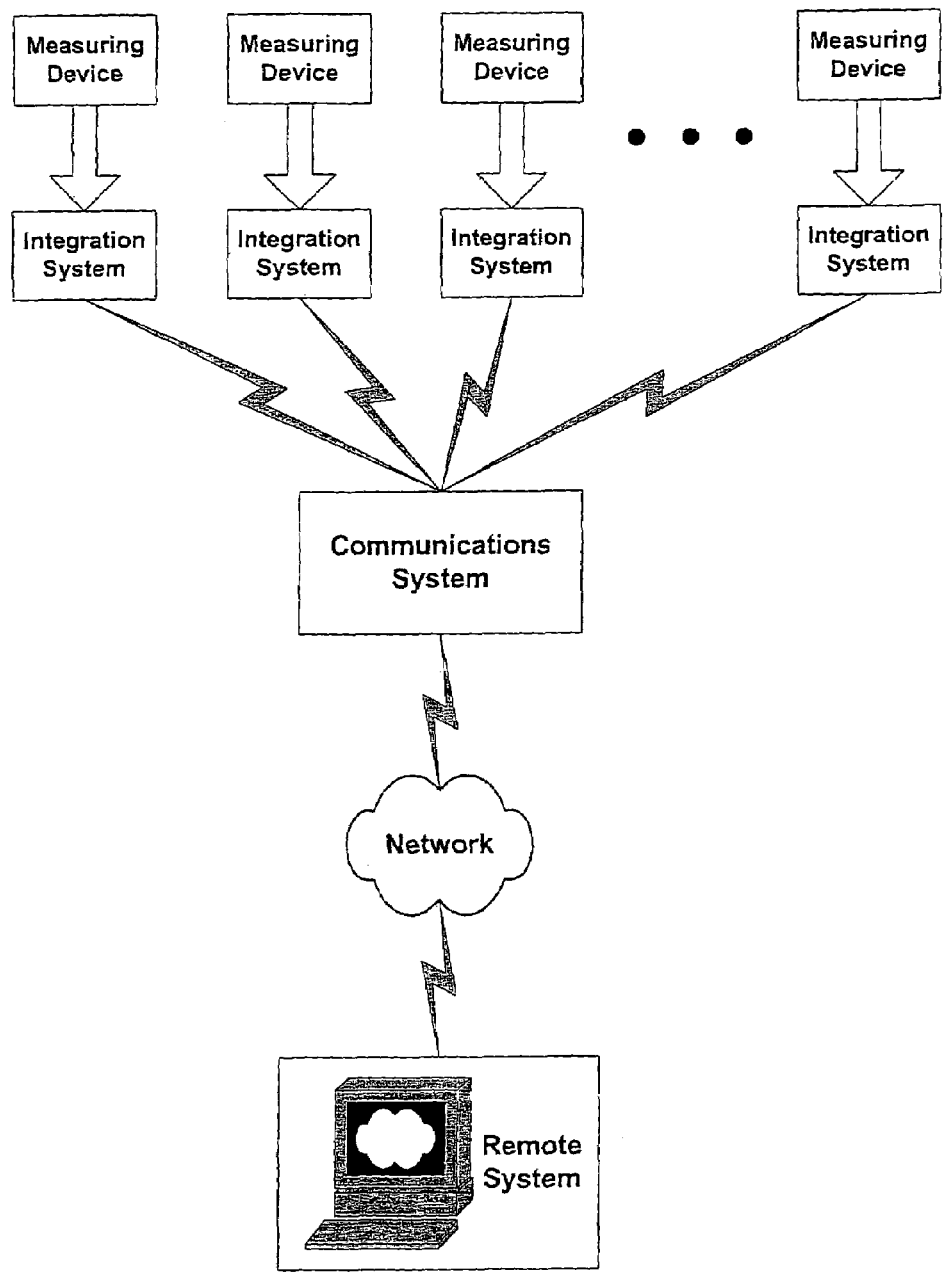
FIG. 3 is a block diagram of the system according to another preferred embodiment.

FIG. 3 illustrates how such a system can be configured. According to a preferred embodiment, a plurality of measuring devices are provided. Each measuring device is connected to an integration system, which is adapted to extract data from the associated measuring device as explained above with reference to FIG. 1. After a measurement is taken by a measuring device, the corresponding integration system then adds the unique device and user IDs to the data, formats it, and transmits it to a central communications system. Upon receiving a measurement from an integration system, the communications system transmits the data to the remote system via the network, as described above with reference to FIG. 1.

While the invention is susceptible to various modifications and alternative forms, specific examples thereof have been shown in the drawings and are herein described in detail. It should be understood, however, that the invention is not to be limited to the particular form disclosed, but to the contrary, the invention is to cover all modifications, equivalents, and alternatives falling within the spirit and scope of the appended claims.

What is claimed is:

1. A system for collecting and transmitting medical and health-related data of at least one user over the Internet, the system comprising:

a warfarin monitor adapted to measure at least one physiological attribute of a user, comprising:

a digital display adapted to display the physiological attribute measurement of the user; and a processor adapted to output a first signal to the digital display, wherein the first signal is related to the physiological attribute measurement of the user;

an integration system adapted to acquire the first signal from the measuring warfarin monitor such that the first signal is not degraded causing the digital display to read an incorrect value, and adapted to convert the first signal into a second signal for wireless transmission over a network;

a communications system adapted to wirelessly transmit the second signal over the network; and a remote system communicatively coupled to the network and adapted to receive the second signal.

2. The system of claim 1, wherein the integration system is coupled to the warfarin monitor in parallel with the processor and the display.

3. The system of claim 1, wherein the integration system is coupled to the warfarin monitor in series with the processor and the display.

4. The system of claim 1, wherein the integration system is adapted to add a unique device identifier to the second signal, the device identifier uniquely identifying the warfarin monitor.

5. The system of claim 4, wherein the communications system is adapted to encode the second signal for transmission over the network.

6. The system of claim 5, wherein the remote system comprises:
- a computer system adapted to extract from the second signal the measured physiological attribute and the device identifier; and
- a database;

wherein the computer system populates the database with the measured physiological attribute and device identifier.

7. The system of claim 6, wherein the integration system adds a unique user identifier to the second signal, and wherein the computer system extracts the user identifier from the encoded second signal and populates the database with the user identifier.

8. The system of claim 1, wherein the integration system includes a second display for visually representing the physiological attribute as indicated by the first signal.

9. The system of claim 1, wherein the second signal is a text string.

10. The system of claim 1, wherein the communications system is adapted to encode the second signal for transmission over the network.

11. The system of claim 1, wherein the integration system adds a unique user identifier to the second signal.

12. The system of claim 1, wherein the communications system is adapted to receive a receipt message wirelessly transmitted from the remote system after the remote system receives the second signal.

13. The system of claim 1, wherein the integration system and the communications system are built on a same second processor.

14. The system of claim 1, further comprising a web-based portal adapted to allow users to access the data over the network.

* * * * *